April 13, 1976
G. H. ODIER
PRUNE TREE
Filed Dec. 23, 1974
Plant Pat. 3,862
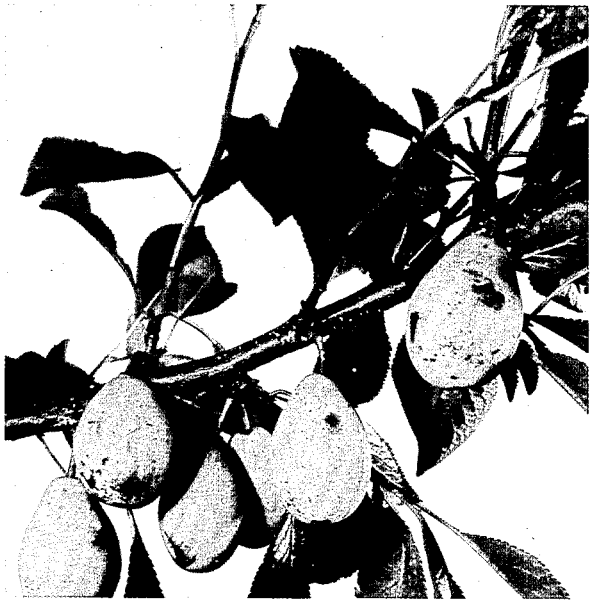
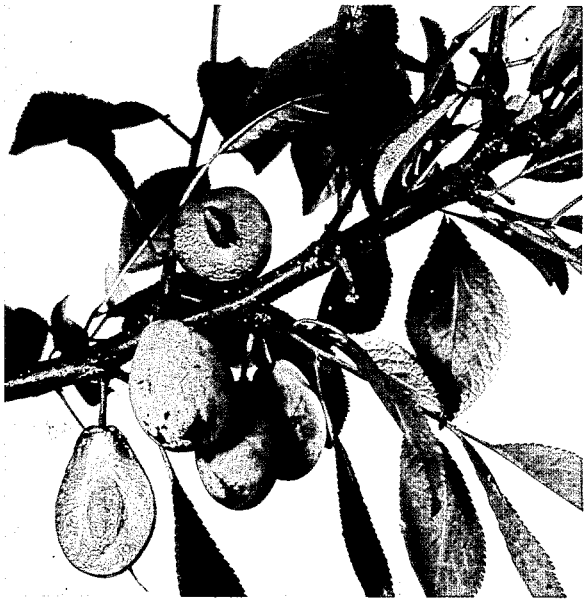

United States Patent

Plant Pat. 3,862

Patented Apr. 13, 1976

3,862

PRUNE TREE

Georges H. Odier, Lot-et-Garonne, France, assignor to Dave Wilson Nursery, Hughson, Calif.

Filed Dec. 23, 1974, Ser. No. 535,991

Int. Cl. A01h 5/03

U.S. Cl. Plt—38 1 Claim

ABSTRACT OF THE DISCLOSURE

A prune tree, of French type, which is large, medium vigorous, upright, dense, vase-formed, hardy, foliated with an above average number per spur of medium size, ovate, abruptly pointed, thick, rugose leaves, and a regular and very productive bearer of early ripening, medium size, symmetrical, oblong, clingstone fruit having dark blue skin and yellow flesh.

BACKGROUND OF THE VARIETY

As an agricultural engineer and an orchardist, it is my practice to maintain my orchard, located at Le Temple Sur Lot, France, under continuing observation, and—during an inspection thereof—I discovered the present variety.

ORIGIN OF THE VARIETY

The present variety of prune tree originated as a natural limb mutation on a normal Agen prune tree growing in my orchard located as aforesaid. On an occasion when inspecting the trees in such orchard, I observed that a limb of one tree bore fruit which had ripened substantially earlier than the fruit on other limbs. Upon such discovery of said mutation limb, I determined to undertake asexual reproduction of such mutation, and which reproduction was thereafter accomplished.

ASEXUAL REPRODUCTION OF THE VARIETY

The present variety of prune tree was first asexually reproduced by me, in my nursery at Le Temple Sur Lot, France, by spring budding as well as grafting on a mature prune tree, and such reproduction ran true to the original mutation (parent) limb in all respects.

SUMMARY OF THE VARIETY

The present variety of prune tree is large, medium vigorous, upright, dense, vase-formed, hardy, foliated with an above average number per spur of medium size, ovate, abruptly pointed, thick, rugose leaves, and a regular and very productive bearer of early ripening, medium size, symmetrical, oblong, clingstone fruit having dark blue skin and yellow flesh; the variety, in comparison with the normal Agen prune tree (e.g., Ente 707), being more compact and more upright in tree growth, and the fruit ripening about eight to ten days earlier with no fruit fall before the harvest, almost all fruit being harvested at the same time, and the fruit having a smaller stone and a higher sugar content.

BRIEF DESCRIPTION OF THE DRAWING

The drawing is an illustration, by photographic reproduction in color, showing—in one view—a twig with leaves and fruit, and—in another view—the same but with certain fruit cut to expose the flesh and stone.

DESCRIPTION OF THE VARIETY

The botanical details of this new and distinct variety of prune tree are as follows:

Tree:
- *Size.*—Large.
- *Vigor.*—Medium.
- *Growth.*—Upright.

- *Density.*—Dense. More compact than normal Agen prune tree.
- *Form.*—Vase-formed.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Stocky.
- *Texture.*—Medium.
- *Color.*—Brown—dull.

Lenticels:
- *Number.*—Numerous.
- *Size.*—Medium.

Leaves:
- *Size.*—Medium. Average length—80 mm. Average width—55 mm.
- *Form.*—Ovate. Abruptly pointed.
- *Thickness.*—Thick.
- *Color.*—Dark green.
- *Texture.*—Rugose.
- *Average number of leaves.*—4 to 6 leaves per spur as compared to 3 or 4 of the normal Agen prune tree.
- *Margin.*—Crenate.
- *Petiole.*—Medium length—average 17 mm. Medium thick.
- *Glands.*—Average number—usually 1; rarely 2. Opposite. Small. Globose. Green. Positioned mostly on blade.
- *Stipules.*—Average number—2 at the base of the leaves.

Flower buds:
- *Hardiness.*—Hardy.
- *Size.*—Small.
- *Length.*—Short.
- *Form.*—Conic. Free.
- *Pubescence.*—Pubescent.

Flowers:
- *Blooming period.*—Date of first bloom—March 31. Date of full bloom—April 10. Medium, as compared with other varieties; substantially with normal Agen prune tree.
- *Size.*—Medium—30 mm.
- *Color.*—White.

Fruit:
- *Maturity when described.*—Eating ripe.
- *Date of first picking.*—August 28.
- *Date of last picking.*—September 9. About 8 to 10 days before normal Agen prune tree.
- *Size.*—Variable. Medium. Average diameter axially—50 mm. Average transversely in suture plane—35 mm. Stem—20 mm.
- *Form.*—Variable. Synmmertical. Oblong. Lightly compressed toward suture.
- *Weight.*—Average—35 gr.
- *Suture.*—Distinct. Extends from base to beyond apex, with slight depression beyond pistil point.
- *Ventral surface.*—Rounded slightly.
- *Lips.*—Equal.
- *Cavity.*—None.
- *Base.*—Truncate. Oblique.
- *Apex.*—Depressed.

Skin:
- *Thickness.*—Medium.
- *Texture.*—Tender.
- *Flavor.*—Astringent.
- *Tenacity.*—Free.
- *Tendency to crack.*—Slight—none in dry season.

*Color.*—Deep burgundy (56–J–8—Maerz and Paul Dictionary of Color).
*Down.*—Wanting.
*Bloom.*—Silver-grey (38–E–2 — Maerz and Paul Dictionary of Color).

Flesh:
*Color.*—Yellow-green (14–L–3 — Maerz and Paul Dictionary of Color). Surface of pit cavity—Yellow.
*Amygdalin.*—Wanting.
*Juice.*—Rich.
*Texture.*—Medium. Melting.
*Fibers.*—Tender.
*Ripens.*—Evenly.
*Flavor.*—Mild. Delicate.
*Aroma.*—Pronounced.
*Eating quality.*—Best.

Stone:
*Type.*—*Cling.* Adheres to flesh over entire surface.
*Size.* — Medium, but smaller than normal Agen. Average length — 2.451 cm. Average breadth—1.298 cm. Average thickness—0.861 cm.
*Form.*—Elliptical.
*Base.*—Oblique.
*Hilum.*—Narrow.
*Apex.*—Rounded.
*Sides.*—Equal.
*Surface.*—Irregularly furrowed near base.
*Ridges.*—Continuous.
*Pits.*—Wanting.
*Ventral edge.*—Thick.
*Dorsal edge.*—Full.

*Color.*—Light brown.
*Tendency to split.*—None.

Use: Culinary.
Canning.
Drying.

Keeping quality: Medium.
Resistance to insects and diseases: Medium.
Shipping quality: Medium.

The prune tree and its fruit herein described may vary in slight detail due to climatic and soil conditions under which the variety may be grown; the present description being of the variety as grown in an agricultural area near Le Temple Sur Lot, France.

I claim:

1. A new and distinct variety of prune tree, substantially as illustrated and described, which is large, medium vigorous, upright, dense, vase-formed, hardy, foliated with an above average number per spur of medium size, ovate, abruptly pointed, thick, rugose leaves, and a regular and very productive bearer of early ripening, medium size, symmetrical, oblong, clingstone fruit having dark blue skin and yellow flesh; the variety, in comparison with the normal Agen prune tree (e.g., Ente 707), being more compact and more upright in tree growth, and the fruit ripening about eight to ten days earlier with no fruit fall before the harvest, almost all fruit being harvested at the same time, and the fruit having a smaller stone and a higher sugar content.

No references cited.

ROBERT E. BAGWILL, Examiner